(12) United States Patent
Santos et al.

(10) Patent No.: US 6,348,217 B1
(45) Date of Patent: Feb. 19, 2002

(54) METHOD FOR PREPARING STABLE BLEACHED SHELLAC

(75) Inventors: Stephen A. Santos, Cumberland, RI (US); Joseph F. Cotter, Sr., South Attleboro; Margaret M. McWeeney, East Boston, both of MA (US)

(73) Assignee: Mantrose-Haeuser Co. Inc., Attleboro, MA (US)

( * ) Notice: Subject to any disclaimer, the term of this patent is extended or adjusted under 35 U.S.C. 154(b) by 0 days.

(21) Appl. No.: 09/632,926

(22) Filed: Aug. 4, 2000

(51) Int. Cl.[7] .............................. A61K 9/34; C09F 1/00
(52) U.S. Cl. ..................... 424/481; 530/201; 524/77; 524/220; 524/366; 424/485; 424/497; 424/500
(58) Field of Search ........................... 530/201; 524/77, 524/220, 366; 424/481, 485, 497, 500

(56) References Cited

U.S. PATENT DOCUMENTS 5,268,406 A * 12/1993 Catena et al. ............... 524/389
5,567,438 A * 10/1996 Cook .......................... 424/474

OTHER PUBLICATIONS

Declaration of Steve Santos dated Mar. 13, 2001.

* cited by examiner

*Primary Examiner*—Samuel A. Acquah
(74) *Attorney, Agent, or Firm*—Calfee, Halter & Griswold LLP

(57) ABSTRACT

A stable bleached shellac and an improved method for making stable bleached shellac is provided which involves precipitating bleached stable shellac from a pre-shellac solution at a pH of from 5.0 to 6.8, preferably from 5.0 to 6.5, most preferably from 5.0 to 6.0. The stable particulate shellac and the stable shellac solution, have a longer shelf life than conventional shellac. The stable shellac solution is comprised of solubilized particulate shellac in a solvent, most preferably ethanol. The stable particulate shellac and the stable shellac solution have a pH of from 4 up to less than 5 or from 5.0 to 6.8, more preferably from 5.0 to 6.5, even more preferably from 5.0 to 6.3, most preferably from 5.0 to 6.0.

37 Claims, No Drawings

METHOD FOR PREPARING STABLE BLEACHED SHELLAC

BACKGROUND OF THE INVENTION

Shellacs have been used as a coating for a variety of substrates for many years. Shellac is typically stored and transported in a dry, solid form under refrigeration. The particulate solid shellac is typically then solubilized in solvent, typically alcohol, prior to use. However, particulate leached shellac is quite reactive. The particulate bleached shellac is not storage stable; it has a short shelf life when exposed to ambient temperature. At ambient temperatures, particulate bleached shellac hardens within days to form a solid block; over time the shellac in the block will also begin to polymerize. If the particulate bleached shellac is exposed to heat during storage or shipping, the polymerization is accelerated.

A hardened un-polymerized or partially polymerized block of shellac may be reclaimed by grinding the block into a powder, and then solubilizing the powder in a solvent. However, the shellac solution must be strained to remove insoluble polymerized shellac solids. The straining step is a time consuming process. Moreover, if the shellac block has substantially polymerized, the shellac is no longer soluble, and even if ground, it is no longer salvageable.

Storing and shipping bleached shellac in solution, as opposed to in particulate form, does not solve the storage problems since shellac solutions also have a limited shelf life, typically one year at ambient temperature. When an aged bleached shellac solution is applied to a substrate, it will not harden into a desirable coating but instead only forms a soft, tacky film. Various compounds have been employed as additives to shellac solutions to increase shelf life. Unfortunately, such compounds typically increase the viscosity, affect the drying time, or affect the functional properties of the shellac.

It would be desirable to have a storage stable, bleached shellac which resists polymerization.

SUMMARY OF THE INVENTION

The present invention provides a bleached stable shellac and an improved method for making bleached stable shellac which involves precipitating bleached stable shellac from a pre-shellac solution at a pH of from 5.0 to 6.8, preferably from 5.0 to 6.5, most preferably from 5.0 to 6.0. As used herein, the term "stable shellac" refers collectively to a stable particulate shellac and a stable shellac solution made from such stable particulate shellac. The stable particulate shellac and the stable shellac solution, have a longer shelf life than conventional shellac. The stable particulate shellac may be stored longer at ambient temperatures and elevated temperatures with minimal or no polymerizing. Upon storage the stable particulate shellac is more resistant to hardening, that is, blocking, than conventional shellac. Significantly, when blocked stable shellac is ground and re-solubilized, there is little need for straining because there is minimal polymerization. The stable shellac solution is comprised of solubilized particulate shellac in a solvent, preferably a volatile organic solvent, even more preferably an alcohol, more preferably ethanol, most preferably 190 proof ethanol.

The stable particulate shellac and the stable shellac solution have a pH of from 4 up to less than 5 or from 5.0 to 6.8, more preferably from 5.0 to 6.5, even more preferably from 5.0 to 6.3, most preferably from 5.0 to 6.0. Where the de-lipidized bleached, stable shellac solution has a pH of from 5.0 to 6.8, it is characterized in that when it is heated to 100° F. for 6 weeks, the pH drops less than 15%, more preferably not greater than 13%, most preferably not greater than 12%.

Where the lipidized, bleached stable shellac solution has a pH of from 5.0 to 6.8, it characterized in that when it is heated to 100° F. for 6 weeks, the pH drops less than 30%, more preferably not greater than 20%, most preferably not greater than 18%.

Where the bleached stable shellac solutions are aged whether over time or in simulated conditions, the pH of both the de-lipidized and lipidized bleached stable shellac solutions tend to drop. When aged, lipidized stable shellac alcohol solution having an initial pH up to less than 5.0, is heated for 30 days at 40° C., the pH tends to drop, to preferably not lower than 3.7, more preferably not lower than 3.8.

When aged de-lipidized stable shellac alcohol solution having an initial pH up to less than 5.0 is heated for 30 days at 40° C., the pH tends to drop, to preferably not lower than 4.2, more preferably not lower than 4.3.

The stable shellac and an acid number of preferably from 65 to 91, more preferably 69 to 85. Once coated and dried, the aged stable shellac solution provides a harder coating than aged conventional shellac solutions.

The present invention also relates to objects coated with the stable shellac.

DETAILED DESCRIPTION OF THE INVENTION

The present invention provides a stable shellac and an improved method for making stable shellac which involves precipitating stable particulate shellac from a pre-shellac solution at a pH of from 5.0 to 6.8, preferably from 5.1 to 6.5; most preferably from 5.2 to 5.5 such pH is higher than conventional methods which are typically at a pH of from 4.1 to 4.5. The resulting stable particulate shellac, and stable shellac solution made from such stable particulate shellac, are more storage stable and have a longer shelf life than conventional shellac. The stable particulate shellac may be stored longer at ambient temperatures and at elevated temperatures with minimal polymerizing. Once coated on a substrate and dried, the aged stable shellac solution provides a harder shellac coating than aged conventional shellac solutions.

Method of Making Stable Particulate Shellac

A liquid pre-shellac is provided. Methods for making liquid pre-shellac are outside the scope of this invention. Conventional methods for making pre-shellac are described in a variety of publications, such as, for example: *Chemistry of Lac*, by P. K. Bose, D. Sc. F. N. I., Y. Sankaranarayanan, M. Sc., S. C. Sen Gupta, M. Sc., Indian Lac Research Institute, (1963); Shellac, Angelo Brothers Ltd., Cossipore, Calcutta, India, (1965); *Kirk-Othmer Encyclopedia of Chemical Technology*, 3$^{rd}$ Edition, Col. 20 (M. Grayson, ed.) Wiley, N.Y. (1982); and *Encyclopedia of Polymer Science and Technology*, Vol. 12 (N. M. Bikales, ed.) Interscience, New York (1970).

Typically a liquid pre-shellac is made by obtaining seedlac, an insect secretion, which is commercially available, removing the debris, and dissolving the seed lac in an alkali such as sodium carbonate to provide a liquid pre-shellac. The liquid pre-shellac is bleached by any of a variety of conventional techniques known in the art. For example, sodium hypochlorite at up to 25% active on shellac weight, is added for several hours, at ambient temperature to bleach the liquid pre shellac. If desired, the liquid pre-shellac is then "de-waxed", that is, refined, by techniques known in the art. Typical refining procedures involve filter pressing through diatomaceous earth to remove wax. The resulting liquid pre-shellac is thus described as refined or unrefined.

The method of making stable particulate shellac of the present invention involves precipitating solid stable shellac from the pre-shellac solution by acidifying the pre-shellac solution at a pH range of 5.0 or higher than 5.0, preferably from 5.0 to 6.8, preferably from 5.0 to 6.5 most preferably 5.0 to 6.0, preferably using a mineral acid such as, for example, hydrochloric acid or sulfuric acid. Organic acids, such as citric acid are also suitable.

It has been discovered that the pH range at which the shellac is precipitated is critical. It has been discovered that at a pH above 6.8 much of the shellac remains in solution and thus precipitating at such a pH results in excessive yield loss. Precipitating at as high as 5.5 is not highly preferred because it has been found that it is difficult to remove water from the shellac. If the shellac is precipitated at a pH below 5.0, the shellac will have the short shelf life that plagues conventional shellacs. Thereafter the stable shellac precipitate, which is typically in slurry form, is preferably fused, that is "hanked" to a soft viscous mass, such as with a hot water bath, and then water preferably is removed, such as by squeezing through rollers. Then the fused, stable shellac precipitate is preferably cooled to harden the shellac, and preferably ground and air dried to preferably from 3% to 6% water content. Good results have been obtained by hanking at from 75° C. to 85° C. The stable shellac then is preferably ground and dried using conventional techniques. After grinding, the stable particulate shellac is preferably further dried to preferably 3% to 6% water content, to again provide the stable particulate shellac.

The stable shellac solution is prepared by combining the stable particulate shellac with a solvent, preferably denatured ethanol, to form from a 5% to 60% solution.

The Stable Particulate Shellac

The moisture content of the bleached stable particulate shellac is comparable to that of conventional shellac. Preferably the Official Moisture content of the stable shellac is not greater than 6%; typically it is 1% to 6%, more preferably it is from 3% to 5%. Preferably the wax content of the refined stable shellac, is from 0% to 0.5%, more preferably from 0.05% to 0.2%. Preferably the wax content of unrefined stable shellac is from 2% to 6% more preferably from 3% to 5.5%.

The term "de-lipidized" as used herein, means a bleached shellac having a wax content of less than 0.5% by weight. The term "lipidized" as used herein, means a bleached shellac having a wax content of greater than or equal to 0.5% by weight.

The Gardner Color number of the bleached stable particulate is determined by preparing a 35% by weight shellac solution in denatured alcohol, 190 proof, and measured the Gardner number according to ASTM Method D1544 1980. The Gardner Color number of such solution is preferably less than 18, preferably less than 9. The Gardner Color number of such solution is preferably from 4 to 18, more preferably from 5 to 9.

Bleached stable particulate shellac has acid number of preferably from 65 to 91, more preferably 69 to 85. When bleached stable particulate shellac is stored at about 55° F. or less, there is little if any change in acid number.

Polymerization Time

The polymerization time of bleached stable particulate shellac, is preferably greater than 10 minutes, more preferably greater than 15 minutes, even more preferably greater than 25 minutes, most preferably greater than 40 minutes. The polymerization time of fresh bleached stable particulate shellac, is preferably from 10 to 40 minutes, more preferably from 15 to 40 minutes, most preferably from 20 to 40 minutes. When the stable particulate shellac is heated for 3 days at 50° C., the polymerization time of the bleached stable particulate shellac is preferably from 10 to 30 minutes, more preferably from 15 to 30 minutes. The percent change in polymerization time between fresh bleached stable particulate shellac and bleached stable particulate shellac when heated at 50° C. for 3 days is from about 10% to 40%. As used herein, the term "fresh shellac" means shellac that is less than 31 days old.

Polymerization time is measured according to the methods described in *"Shellac—Official Methods of Analysis, Standards, Specifications and General Information on Shellac and Bleached Shellac"*, approved by The American Bleached Shellac Manufacturers' Association, Inc. and the United States Shellac Importers' Association, Inc., New York, copyright 1957, American Bleached Shellac Manufacturers' Association, Inc., section 3.22, pages 19–25, hereinafter referred to as "AUSSIA Polymerization Test".

Polymerization time is an indicator of the solubility of the particulate shellac and an indicator of the shelf life of the shellac. Polymerization time is also an indicator of the extent of polymerization of the particulate shellac. The longer the polymerization time, the more soluble and less polymerized the shellac sample is. The stable particulate shellac samples of the examples showed significantly longer polymerization times than the comparative examples after heating.

The total chloride content of bleached stable shellac is preferably from 1% to 5%, more preferably from 1.5% to 3%.

The Stable Shellac Solution

A stable shellac solution is prepared by mixing the stable particulate shellac with a solvent such as a volatile organic solvent or with water. Suitable volatile organic solvents are, for example, acetone, ethylene glycol butyl ether, methyl propyl carbinol, alcohols, including monohydric, dihydric and polyhydric alcohols, and propylene glycol, ethylene glycol, and diethylene glycol. The preferred alcohols are methanol, ethanol and isopropyl alcohol. Good results have been obtained using 35% by weight, stable precipitate shellac in solution.

To form an aqueous stable shellac solution, a base is added to the water and the stable shellac to provide the solution with a pH 7 or higher preferably a pH of 7 to 9.0. Suitable bases are for example sodium hydroxide, ammonium hydroxide, potassium hydroxide, and morpholine. By "aqueous stable shellac solution" it is meant that there is at least 60% by weight water in the solution. At pH of 7 or greater a shellac and a sodium shellactate salt is formed.

pH

The pH of fresh stable shellac alcohol solution specifically a 35% solution in 190 proof denatured ethanol, is preferably from 5.0 to 6.8, more preferably from 5.1 to 6.5, most preferably from 5.2 to 6.3. Stable shellac solutions which are not 35% stable particulate shellac solution, may be diluted or concentrated or dried and re-dissolved, to provide a 35% solution to conduct measurements, particularly pH. Stable shellac solutions which are not 190 proof denatured ethanol solutions are evaporated and re-dissolved in 190 proof denatured ethanol for measurements particularly pH measurements. Thus pH values referred to herein are in 190 proof denatured ethanol unless other wise noted.

When stable shellac alcohol solution having an initial pH of from 5.0 to 6.8 is aged, the pH of the bleached stable shellac alcohol solution tends to drop. For example, when lipidized, stable shellac alcohol solution having an initial pH of from 5.0 to 6.8 is aged such as by heating for 6 weeks at 100° F., the pH tends to drop preferably not greater than 30%, more preferably not greater than 20%, most preferably not greater than 18%.

When de-lipidized, stable shellac alcohol solution having an initial pH of from 5.0 to 6.8 is aged such as by heating for 6 weeks at 100° F, the pH tends to drop preferably not greater than 15%, more preferably not greater than 13%, most preferably not greater than 12%.

When aged, lipidized stable shellac alcohol solution having an initial pH up to less than 5.0, is heated for 30 days at 40° C., the pH tends to drop, to preferably not lower than 3.7, more preferably not lower than 3.8.

When aged de-lipidized stable shellac alcohol solution having an initial pH up to less than 5.0 is heated for 30 days at 40° C., the pH tends to drop, to preferably not lower than 4.2, more preferably not lower than 4.3.

Acid Number

The acid number of stable shellac alcohol solution specifically a 35% solution, is preferably from 63 to 91, more preferably from 69 to 85, most preferably from 72 to 79. The acid number of fresh stable shellac alcohol solution specifically a 35% solution, is preferably from 65 to 91, more preferably from 69 to 85, most preferably from 72 to 79.

When the stable shellac alcohol solution is heated for 3 months at 40° C., the acid number of the bleached stable shellac alcohol solution is preferably from 63 to 81, more preferably from 67 to 84. The change in acid number between fresh stable shellac alcohol solution and stable shellac alcohol solution heated at 50° C. for 3 months is preferably from 1% to 10%, more preferably from 2 to 6%.

Dry Time

Generally, the drying time of stable shellac alcohol solution specifically a 35% solution, at 20° C. and 50% relative humidity, is preferably less than 35 minutes, more preferably less than 30 minutes, most preferably less than 20 minutes. The drying time of fresh stable shellac alcohol solution specifically a 35% solution, is preferably less than 20 minutes, preferably from 12 to 20, more preferably from 12 to 17, most preferably from 12 to 15 minutes. When the stable shellac alcohol solution is heated for 3 months at 40° C., the drying time of the bleached stable shellac alcohol solution is preferably from 15 to 30, more preferably from 15 to 20 minutes. The change in drying time between fresh stable shellac alcohol solution and stable shellac alcohol solution heated at 40° C. for 3 months is from about 10% to 100%.

The stable shellac solution is preferably free of aminomethylpropanol, also referred to herein as "AMP". By "free of aminomethylpropanol" it is meant that the stable shellac solution contains less than 0.05% aminomethylpropanol by weight of shellac solids.

The stable shellac solution is preferably free of amine. By "free of amine" it is meant that the stable shellac solution contains less than 0.05% amine by weight of shellac solids. The stable shellac solution preferably contains less than 1%, more preferably less than 0.5%, even more preferably less than 0.2%, most preferably less than 0.1% free hydroxyl ions, by weight of shellac solids.

The Shellac Coating

The stable shellac solution when dried, provides a hard protective coating, useful in the same ways as is conventional shellac, such as for example, as a glaze, varnish, and sealer. The stable shellac solution is applied using conventional techniques used to apply conventional shellac such as brushing, dripping, spraying, or ladling. The solvent in the stable shellac solution evaporates to leave a hard stable shellac coating. The stable shellac, like conventional shellac is useful to coat a variety of substrates; for example: food items such as fruit and vegetables where the shellac coating is useful to prevent dehydration particularly of citrus fruits; confections, such as for example, candy and gumballs; pharmaceuticals and nutritional supplements, such as tablets, capsules, and pills; and architectural or building materials such as wood, masonry, fiber, vinyl, and metal. Shellac is particularly useful as a primer paint or primer paint component for wood. The novel stable shellac solution offers the advantage of providing a harder coating when dried than conventional shellac.

Hardness

The hardness of stable shellac alcohol solution specifically a 35% alcoholic solution, is preferably from 100 to 200, more preferably from 120 to 200, most preferably from 150 to 200 Konig units. The hardness of fresh stable shellac alcohol solution specifically a 35% solution, is preferably from 100 to 200, more preferably from 120 to 200, most preferably from 150 to 200 Konig units. When the stable shellac alcohol solution is heated for 3 months at 40° C., the hardness of the bleached stable shellac alcohol solution is preferably from 80 to 160, more preferably from 120 to 160 Konig units. The change in hardness between fresh stable shellac alcohol solution and stable shellac alcohol solution heated at 40° C. for 3 months is from about 15 to 30%.

EXAMPLE 1

A stable particulate shellac was prepared as follows. A solution of bleached, unrefined pre-shellac was provided. Then the stable shellac was precipitated from the solution by the addition of 0.5N sulfuric acid, to a pH of 5.2–5.3, and the solids washed with water, hanked, crushed, then dried in a rotary air dryer oven at 120° F. for 6 hours to provide a stable particulate shellac. The stable particulate shellac was then ground through an Abbe and Hammer mill to an maximum particle size of 10 mesh, with 7% particles at maximum.

EXAMPLE 1A

A stable particulate shellac was prepared as in example 1, except that the stable shellac was precipitated at a pH of 5.2.

EXAMPLE 2

A stable particulate shellac was prepared as in example 1, except that a solution of bleached, refined pre-shellac was provided.

EXAMPLE 3

A stable particulate shellac was prepared as in example 1, except that a solution of semi-bleached, refined pre-shellac was provided.

EXAMPLE 4

A stable particulate shellac was produced as in Example 1, except that the stable shellac was precipitated at pH 5.1.

EXAMPLE 5

A stable particulate shellac was produced as in Example 2, except that the stable shellac was precipitated at pH 5.1.

EXAMPLE 6

A stable particulate shellac was produced as in Example 3, except that the stable shellac was precipitated at pH 5.1.

EXAMPLE 7

A stable particulate shellac was produced as in Example 1, except that it was not hanked, and the stable shellac was precipitated at pH 6.2.

EXAMPLE 8

A stable particulate shellac was produced as in Example 2, except that the stable shellac was precipitated at pH 6.2.

EXAMPLE 9

A stable particulate shellac was produced as in Example 3, except that the stable shellac was precipitated at pH 6.2.

EXAMPLE 10

A stable particulate shellac was produced as in Example 1, except that the stable shellac was precipitated at pH 5.6.

EXAMPLE 11

A stable particulate shellac was produced as in Example 2, except that the stable shellac was precipitated at pH 5.6.

EXAMPLE 12

A stable particulate shellac was produced as in Example 3, except that the stable shellac-was precipitated at pH 5.6.

EXAMPLE 13 70795

A stable particulate shellac was produced as in Example 1.

EXAMPLE 14

A stable particulate shellac was produced as in Example 1.

COMPARATIVE EXAMPLE A

A particulate shellac was produced as in Example 1, except that the shellac was precipitated at a pH of 4.3 to 4.6.

COMPARATIVE EXAMPLE B

A particulate shellac was produced as in Example 2, except that the shellac was precipitated at a pH of 4.3 to 4.6.

COMPARATIVE EXAMPLE C

A particulate shellac was produced as in Example 3, except that the shellac was precipitated at a pH of 4.3 to 4.6.

COMPARATIVE EXAMPLE D (UNBLEACHED)

A particulate shellac was obtained which is not bleached, only decolored and refined.

A stable shellac of Example 1A had a glass transition of 57.2° C. and melting points at 62.4° C., 78.0° C. and 86.0° C. The stable shellac of two additional batches of Example 1A had a glass transition of 55.9° C. and melting points at 72.7 and 78.7° C., and had a glass transition of 54.6° C. and melting points at 61.4° C., 75.0° C., 87.0° C. and 100.4° C. The refined stable shellac of Example 2 had a glass transition of 52.9° C. and melting points at 54.0 and 73.7° C.

The shellac of Comparative Example A had a glass transition of 49.0° C. and melting points at 77.0° C. and 87.3° C. The shellac of Comparative Example B had a glass transition of 55.1° C. and melting points at 66.7° C. and 74.7° C. The shellac of an additional batch of Comparative Example A had a glass transition of 59.5° C. and melting points at 63.4° C., 76.7° C. and 87.0° C. The shellac of an additional batch fo Comparative Example A had a glass transition of 63.4° C. and melting points at 43.4° C., 76.7° C. and 87.4° C.

Evaluation

Stable particulate shellacs of the above examples were evaluated; also stable shellac solutions of the stable particulate shellac of the examples were prepared and evaluated. Selected stable shellac solutions were coated onto a substrate, typically glass, and the dried coatings or films were evaluated.

Stable shellac samples which are listed as fresh were 1 to days old. The stable particulate shellac of Examples 1 to 3 and the stable shellac solutions made therefrom, were heated in a convection oven to simulated aging.

The stable shellacs of Examples 1, 2 and 3, were evaluated for film hardness according to ASTM D-4366-87 (1987). Standard test methods for hardness of organic coatings by Pendulum Damping Test also referred to as Konig hardness. Stable shellac solutions were prepared by dissolving 4 pounds of stable particulate shellac of Examples 1–3 in 1 gallon denatured alcohol, ½00 proof to provide 35% shellac solution. The stable shellac solutions were stored in a refrigerator at 10° C., or in a 40° C. oven for either 1, 2 or 3 months. Films of about 3 mils thickness were prepared on glass and "cured" for 7 days at 0 ambient temperature. The hardness of the films was determined using a Pendulum Hardness Tester from BYK-Gardner according to ASTM D 4366. The films were placed in the Pendulum Hardness Tester pendulum allowed to pass over the sample lightly touching the surface of the sample. The harder the film, the more passes the arm makes in 1 minute. Thus, softer films have a higher coefficient of friction and reduce the number of passes the swinging arm makes in the same time period. Control shellac solutions were also prepared and evaluated. The results are shown below.

SHELLAC COATING HARDNESS

| Sample Description | Cold aged 1 mo. Hardness (Konig) | Oven aged (40° C.) 1 mo. Hardness (Konig) | Oven aged (40° C.) 2 mo. Hardness (Konig) | Oven aged (40° C.) 3 mo. Hardness (Konig) |
| --- | --- | --- | --- | --- |
| Comparative Ex. A 200 proof | 116 | | 88 | 74 |
| Comparative Ex. A 190 proof | 108 | | 80 | 84 |
| Stable Shellac Ex. 1 200 proof | 100 | | 7 | 69 |
| Stable Shellac Ex. 1 190 proof | 92 | | 81 | 81 |
| Stable Shellac Ex. 1 200 proof | 120 | | 87 | 69 |
| Stable Shellac Ex. 1 190 proof | 126 | | 96 | 90 |
| Comparative Ex. C 200 proof | 178 | 170 | 135 | 118 |
| Comparative Ex. C 190 proof | 189 | 166 | 148 | 118 |
| Stable Shellac Ex. 3 200 proof | 172 | 182 | 160 | 119 |
| Stable Shellac Ex. 3 190 proof | 178 | 166 | 146 | 126 |
| Stable Shellac Ex. 3 200 proof | 178 | 178 | 176 | 151 |
| Stable Shellac Ex. 3 190 proof | 195 | 181 | 146 | 166 |

-continued

SHELLAC COATING HARDNESS

| Sample Description | Cold aged 1 mo. Hardness (Konig) | Oven aged (40° C.) 1 mo. Hardness (Konig) | Oven aged (40° C.) 2 mo. Hardness (Konig) | Oven aged (40° C.) 3 mo. Hardness (Konig) |
|---|---|---|---|---|
| Stable Shellac Ex. 3 200 proof | 164 | 178 | 157 | 145 |
| Stable Shellac Ex. 3 190 proof | 176 | 197 | 173 | 128 |
| Comparative Ex. B 200 proof | 181 | 182 | 140 | 111 |
| Comparative Ex. B 190 proof | 194 | 171 | 144 | 103 |
| Stable Shellac Ex. B 200 proof | 194 | 197 | 167 | 136 |
| Stable Shellac Ex. B 190 proof | 184 | 200 | 157 | 136 |
| Stable Shellac Ex. B 200 proof | 187 | 188 | 164 | 133 |
| Stable Shellac Ex. B 190 proof | 198 | 181 | 143 | 151 |
| Comparative Ex. D (unbleached) 200 proof | 161 | 160 | 150 | 97 |
| Comparative Ex. D (unbleached) 190 proof | 124 | 104 | 108 | 96 |
| Comparative Ex. D (unbleached) 200 proof | 170 | 144 | 99 | 111 |
| Comparative Ex. D (unbleached) 190 proof | 169 | 136 | 102 | 100 |

As can be seen from the above table, on the average, the hardness of the comparative shellac coating decreases upon storage. In contrast, the hardness of the refined stable shellac coating did not significantly decrease over time.

The stable shellacs of examples 1, 2, and 3, were evaluated for film hardness according to ASTM D-4366, *Hardness of Organic Coatings by Pendulum Damping*, 1987. Stable particulate shellac samples were stored in an oven for 1 week at 40° C. Then stable shellac solutions were prepared by dissolving 25 grams stable particulate shellac in 50 ml denatured alcohol, 200 proof. Films of about 3 mil thickness were prepared on glass and cured for 7 days at ambient temperature and 50% relative humidity. The LAC aged one week at 40° C. The films were evaluated as described above. Control shellac solutions were also prepared and evaluated. The results are shown below.

HARDNESS OF FILMS PRODUCED FROM PARTICULATE SHELLAC

| Sample Description | Film Hardness 3 ml film/4 # cut |
|---|---|
| Comp. Ex C | 169 |
| Stable Shellac Ex. 3 | 180 |
| Comp. Ex. B | 160 |
| Stable Shellac Ex. 2 | 161 |
|  | 110 |
| Ex. 4 | 153 |
| Stable Shellac Ex. 1 | 132 |
| Stable Shellac Ex. 1 | 137 |

As can be seen from the above table, on average, the hardness of the stable shellac coating is greater than the aged comparative shellac coatings.

The stable shellacs of Examples 1, 2, and 3, were evaluated for dry time according to ASTM D 1650-76 (Re-approved 1981) *Standard Methods of Testing Shellac Varnish*. Stable shellac solutions 1/200 were prepared by dissolving 4 pounds of particulate shellac in 1 gallon denatured 200 proof alcohol, to provide 35% solids solution and either stored in a refrigerator at 10° C., or stored at ambient temperature or stored in a 40° C. oven, for 3 months. Films of about 3 mils thickness were cast on draw down charts and the time to dry a tack free state as determined by touch was measured. Control shellac solutions were also prepared and evaluated. The results are shown below.

DRY TIME OF SHELLAC SOLUTIONS

| Sample Description | 3 Months at 10° C. (Refrig.) (min.) | 3 Months Ambient (minutes) | 3 Months at 40° C. Oven (minutes) |
|---|---|---|---|
| Comparative Ex. A | 16 | 38 | 57–58 |
| Stable Shellac Ex. 1 | 15 | 15–20 | 30 |
| Stable Shellac Ex. 1 | 15 | 15–20 | 30 |
| Stable Shellac Ex. 1 | 15 | 15–20 | 30 |
| Comparative Ex. C STD | 15 | 20 | 26 |
| Stable Shellac Ex. 3 | 15 | 15 | 17 |
| Stable Shellac Ex. 3 | 15 | 15 | 17 |
| Stable Shellac Ex. 3 | 15 | 15 | 17 |
| Comparative Ex. B | 17 | 21 | 34 |
| Stable Shellac Ex. 2 | 17 | 16 | 19 |
| Stable Shellac Ex. 2 | 17 | 16 | 19 |
| Comparative Ex. A w/AMP | 16 |  | 62 |
| Stable Shellac Ex. 1 w/AMP | 16 |  | 41 |
| Stable Shellac Ex. 1 w/AMP | 16 |  | 41 |
| Stable Shellac Ex. 1 w/AMP | 16 |  | 41 |

As can be seen from the above table, the drying time of the comparative shellac solutions increases upon storage. In contrast, the drying time of the stable shellac coating does not substantially increase over time.

The acid number of Examples 1–3, was determined by tritation according to ASTM D-29 method entitled *Standard Test Methods for Sampling and Testing Lac Resins* 1981 (re-approved 1987). Stable shellac solutions 1/200 were prepared by dissolving 4 pounds of particulate shellac in 1 gallon denatured 200 proof alcohol, to provide 35% solids solution and either: stored for in a refrigerator at 10° C. 1 month or stored in a 40° C. oven, for 1, 2 or 3 months. Control shellac solutions were also prepared and evaluated. The refrigerated sample is the equivalent of a fresh shellac sample. The reduction in acid values was determined by comparing the refrigerated sample to the 3 month values

Acid Number of Shellac Solutions Stored Over Time

| Sample Description | Acid No. one mo. at 40° C. cold | Acid No. one mo. at 40° C. | Acid No. two mo. at 40° C. | Acid No. three mo. at 40° C. | Percent Change in Acid Number |
|---|---|---|---|---|---|
| Comp. Ex. C | 79.3 | 77.1 | 73.8 | 73.7 | 7.1% |
| Stable Shellac Ex. 3 | 74.0 | 73.0 | 70.6 | 72.2 | 2.4% |
| Comp. Ex. B | 83.8 | 80.4 | 73.5 | 71.7 | 14.4% |
| Stable Shellac | 76.6 | 80.6 | 78.7 | 81.0 | 5.7% |

-continued

Acid Number of Shellac Solutions Stored Over Time

| Sample Description | Acid No. one mo. at 40° C. cold | Acid No. one mo. at 40° C. | Acid No. two mo. at 40° C. | Acid No. three mo. at 40° C. | Percent Change in Acid Number |
|---|---|---|---|---|---|
| Ex.2 Comp. Ex. A | 82.7 | 81.3 | 67.2 | 60.7 | 26.6% |
| Stable Shellac Ex. | 76.9 | 79.8 | 74.7 | 74.5 | 3.1% |
| Comp. Ex. D (unbleached) | 73.3 | 72.0 | 68.7 | 70.0 | 4.5% |

As can be seen from the above table, the acid number of the comparative shellac solutions decreases upon storage. In contrast, the acid number of the stable shellac coating does not substantially decrease over time.

The pH of Examples 1–3, was determined in stable shellac solutions 3# which were prepared by dissolving 18 grams stable particulate shellac in 50 ml denatured alcohol, 190 proof, and either: stored at ambient temperatures or stored at 100° F., for 6 weeks. The pH was measured initially and at 6 weeks. The acid number was also determined. Acid value is the number of milligrams of potassium hydroxide required to neutralize one gram of moisture-free lac resin and was determined according to Acid Value test was determined according to ASTM D-29-81 (Re-approved 1987) *Standard Test Methods for Sampling and Testing Lac Resins*, Section 21. Control shellac solutions were also prepared and evaluated. The results are shown below.

CHANGE OF SHELLAC pH OVER TIME

| Shellac Type | pH initial | Acid Value initial | pH of shellac solution stored 6 weeks at 100° F. | Acid Value 6 weeks | Percent change in pH of 6 week from initial |
|---|---|---|---|---|---|
| Comparative Ex. A | 4.36 | 26.1 | 2.25 | 22.9 | −48% |
| Comparative Ex. A w/amp | 4.87 | 26.1 | 2.48 | 25.1 | −49% |
| Stable shellac Ex. 1 w/amp | 5.13 | 23.8 | 4.48 | 24.6 | −13% |
| Stable shellac Ex. 1 | 4.88 | 23.8 | 4.08 | 24.0 | −16% |
| Comparative Ex. B REFINED | 4.76 | 25.4 | 3.23 | 25.2 | −32% |
| Comparative Ex. B w/amp | 5.20 | 25.7 | 4.26 | 25.5 | −18% |
| Stable shellac Ex. 2 W/amp | 5.66 | 23.5 | 5.05 | 24.1 | −11% |
| Stable shellac Ex. 2 | 5.33 | 23.8 | 4.83 | 23.9 | −9% |
| Comparative Ex. C STD - | 5.40 | 25.7 | 3.71 | 25.0 | −31% |
| Comparative Ex. C w/amp | 5.59 | 25.7 | 4.49 | 25.4 | −20% |
| Stable shellac Ex. 3 | 5.59 | 22.6 | 5.08 | 22.9 | −9% |
| Stable shellac Ex. 3 w/amp | 5.40 | 23.8 | 4.85 | 23.9 | −10% |
| Comparative Ex. D (unbleached) | 4.74 | 23.5 | 4.67 | 23.3 | −1% |
| Comparative Ex. D w/AMP (unbleached) | 5.32 | 23.5 | 5.34 | 23.2 | 0% |

Above reported acid values are not corrected for shellac solids content and are thus lower than actual.

As can be seen from the above table, the pH of the comparative shellac solutions decreases upon storage. In contrast, the pH of the stable shellac solution does not substantially decrease over time.

Polymerization time, also referred to as "life time" was determined according to the *"Shellac—Official Methods of Analysis, Standards, Specifications and General Information on Shellac and Bleached Shellac"*, approved by The American Bleached Shellac Manufacturers' Association, Inc. and the United States Shellac Importers' Association, Inc., New York, copyright 1957, American Bleached Shellac Manufacturers' Association, Inc., section 3.22, pages 19–20, hereinafter referred to as "AUSSIA" Polymerization Test.

Five grams of stable shellac was desiccated at 41° C. for either overnight or more than 16 hours. Two grams of the desiccated stable shellac was placed in a tube which was deposited in an oil bath at 150° C. to melt and to polymerize the shellac samples. A glass rod was placed in the tube and twisted by hand. The point at which the glass rod twists back is the end point and indicates that the test material has polymerized. The time elapsed between the point at which the sample was placed in the oil bath and the point at which the sample polymerized is the polymerization time. Control shellac solutions were also prepared and evaluated.

Color Index was determined as described in ASTM D1544-80 entitled Standard test Method for color of Transparent Liquids (Gardner Color Scale) (1980) except either a Gardner-Hellige Varnish Comparator from BYK-Gardner, Silver Spring MD, having color wheel standards, or Lovibond/Gardner Varnish Comparator form Paul N. Gardner Company, Inc., Pompano Beach, FL, was used. Thus glass color wheel standards are employed instead of liquid standards.

POLYMERIZATION TIME OF PARTICULATE SHELLAC STORED AT 40° C.

| Shellac Sample | Polymerization Time Shellac Stored 1 Week 40° C. | Polymerization Time Shellac Stored 2 Weeks 40° C. |
|---|---|---|
| Comparative Ex. C | 8 min. | 0 min. |
| Stable Shellac Ex.3 | 20 min. | 10 min. |
| Comparative Ex. B | 8 min. | 0 min. |

-continued

POLYMERIZATION TIME OF PARTICULATE SHELLAC STORED AT 40° C.

| Shellac Sample | Polymerization Time Shellac Stored 1 Week 40° C. | Polymerization Time Shellac Stored 2 Weeks 40° C. |
|---|---|---|
| Stable Shellac Ex. 2 | 16 min. | 6 min. |
| Comparative Ex. A | 8 min. | 0 min. |
| Repeat Run Stable Shellac Ex.3 | 11 min. | 6 min. |
| Stable Shellac Ex. 1 | 16 min. | 9 min. |

As can be seen from the above table, the polymerization time of the Comparative Examples of shellac decreases upon storage; at two weeks it dropped to 0. In contrast, the polymerization time of the stable particulate shellac decreased to a lesser extent.

Examples 13 and 14 and comparative example A were evaluated for heat storage stability and esterification. Color was determined as described above. The Official Moisture in stable particulate shellac was determined as described in "Shellac—Official Methods of Analysis, Standards, Specifications and General Information on Shellac and Bleached Shellac", approved by The American Bleached Shellac Manufacturers' Association, Inc. and the United States Shellac Importers' Association, Inc., New York, copyright 1957, American Bleached Shellac Manufacturers' Association, Inc., section 3.2a, page 10 hereinafter referred to as "AUSSIA" Official Moisture Test. Briefly, for the moisture test, samples were heated at 41° C. for at least 9 hours, and the stable shellac was removed and measured. The results are shown below in Tables I and II.

TABLE I

| Tests | Comp. A | Comp. A | Comp. A | Ex. 13 | Ex. 14 |
|---|---|---|---|---|---|
| Acid Number | 82.5 | 80.5 | 81.4 | 74.1 | 74.0 |
| Color at 35% solution in alcohol (25 g/50 mls) filtered Lovibond Scale | 2 | — | 1¾ | 2½ | 2½ |
| Gardner Scale | 6 | — | 6 | 7½ | 7 |
| Official Moisture | 5.8 | 5.2 | 4.1 | 4.0 | 3.6 |
| Polymerization Time fresh shellac | 7 min. | 6.20 | 6.30 | 13.30 | 13.0 |
| Gel Time (minutes) fresh shellac | 3.3 | 4.4 | 4.2 | 4.4 | 3.4 |
| Gel Time after 50° C./3 days | 8 m. | 8 m. | 8.4 | 4.5 | 3.2 |
| Polymerization Time after 50° C./3 days | 6:30 | 5:40 | 5:5 | 11 min | 12 min |
| Polymerization Time at 11 Days | no melt | no melt | no melting | gelled within 1 min. | gelled within 1 min. |
| Initial acid number 35% solution* | 83.9 | 82.8 | 81.1 | 74.8 | 76.3 |
| 1 month oven acid number | 80.2 | 76.2 | 75.4 | 74.8 | 76.5 |
| 190 proof cut W/0 AMP Initial acid number | 83.1 | 83.2 | 81.7 | 76.3 | 76.3 |
| 1 month oven acid number | 80.5 | 77.0 | 77.1 | 77.5 | 80.2 |
| 190 proof cut w/AMP Initial acid number | 83.8 | 82.4 | 80.9 | 72.3 | 77.3 |
| 1 month oven acid number | 88.9 | 85.4 | 82.9 | 78.9 | 81.8 |

*4# Cut in 200 proof alcohol

TABLE II

| Tests | Ex. 1 | Comparative Ex. A |
|---|---|---|
| Acid Number | 76.1 | 84.3 |
| Color at 35% solution in alcohol (25 g/50 ml) filtered Lovibond Scale | 1 ¾ | 1 ½ |
| Gardner Scale | 6 | 6 |
| Official Moisture | 1.4% | 4.2% |
| Polymerization Time fresh shellac | 13.4 min | 8 min |
| Gel Time fresh shellac | 10 min | 7 min |
| Acid Number 35% [4# Cut in 1/200] 200 proof alcohol | | |
| Initial Acid Number | 75.1 | 83.1 |
| 1 month oven Acid Number | 74.3 | 74.1 |
| 190 proof alcohol w/o AMP | | |
| Initial Acid Number | 73.0 | 81.6 |
| 1 month oven Acid Number | 75.0 | 74.0 |
| 190 Proof alcohol w/AMP | | |
| Initial Acid Number | 73.8 | 83.7 |
| 1 month oven Acid Number | 76.4 | 81.6 |

The 190 proof alcohol composition contained: 87% ethyl alcohol, 4% methyl alcohol, 2% methyl isobutyl ketone, and 7% water by weight. The 200 proof alcohol composition contained: 94% ethyl alcohol, 4% methyl alcohol, and 2% methyl isobutyl ketone.

As can be seen in the above tables, the acid number is consistently lower in the stable shellac than in the conventional shellac. As noted in table 1, the fresh stable shellac took almost twice as long to polymerize as fresh comparative shellac. Indeed, even after heating, the stable shellac took almost twice as long to polymerize as fresh comparative shellac.

In the 200 proof alcohol solution the comparative shellac exhibited 5–8% degree of esterification; that is, the hydroxyl groups in the alcohol reacted with the COOH groups in the shellac, which in turn reduced the acid number. The two samples of the stable shellac of examples 13 and 14 did not show any signs of esterification, even after 1 month in a 40° C. oven.

Fresh samples of the stable shellac of Example 1 was subjected to dissolution analysis. Samples of the stable shellac of Example 1 was also aged in an oven at 40° C. for 3 days and then subjected to dissolution analysis. The dissolution analysis was conducted at 37° C. unless otherwise noted. A cleaned and dried stirring rod was weighed. The rod was then coated by placing 1–3 drops of the shellac solution on the rod while rotating the rod and tipping it back and forth to obtain an even coating. The rod was then hung vertically, dried for 5 minutes at room temperature, and then hung in a 40° C. oven for 5 minutes. This procedure was repeated, typically about 8 times, until a 10 mg or greater coating of stable shellac was formed on the rod. Then rods were placed in a 40° C. oven for 30 days, then the rods were removed, cooled and weighed. The rods were placed in a solution of buffered saline at pH 7.4 for 30 minutes with very light agitation to dissolve some of the dried resin on the rod. The rods were removed, air dried and then dried overnight 40° C. The rods were cooled and weighed again. The percent difference between the weight of the rod after agitation in the buffered saline and the initial coated rod indicates the percent of resin dissolved. The results, which are averages of three values, are shown below.

TABLE III

Percent of Shellac Dissolved

| SAMPLE | OVERNIGHT AT 40° C. | 30 DAYS AT 40° C. |
|---|---|---|
| Example 1 fresh | 2.2% | 5.3% |
| Example 1 AGED 1 MO | 6.8% | 2.4% |
| Comparative Example A fresh | 4.3% | 4.8% |
| Comparative Example A AGED 1 MO | 38.5% | 16.6% |

The results show that the aged stable shellacs have less change in amount dissolved after aging than the comparative shellac; thus the aged stable shellacs exhibit more stability.

The Biological Oxygen Demand of the effluent from the stable shellac increased. This was due to the soluble fraction of stable shellac remaining in the waste water after precipitation at a higher pH.

Samples of Examples 1, 2, and 3, and Comparative Examples A, B, and C, were aged for 12 months the pH was determined and then the samples were placed in an gravity convection oven for 30 days at 40° C. The samples were removed and the pH determined. The results are shown below.

| Sample | pH 1 year after aging at ambient temp. | pH after 1 year ambient followed by 30 day at 40° C. |
|---|---|---|
| Comparative Ex. B | 3.53 | 2.86 |
| Example 2 | 4.63 | 4.47 |
| Comparative Ex. C | 4.06 | 3.55 |
| Example 3 | 4.54 | 4.42 |
| Comparative Ex. A | 2.35 | 1.97 |
| Example 1 | 4.32 | 3.94 |

As noted above, the 1 year old stable shellac of Examples 1, 2, and 3, showed little drop in pH when oven aged. Notably, the lipidized stable shellac did not drop below 3.7, and the de-lipidized stable shellac did not drop below 4.2. Specifically, the lipidized stable shellac did not drop below 3.94, and the de-lipidized stable shellac did not drop below 4.42.

A Time Release Pill

A time release pill is formed using the stable shellac by providing a sugar bead which is then coated with a thin first layer of stable shellac solution. Preferably while the first layer of stable shellac is still tacky, a pharmaceutical is applied, such as by dusting to the first layer of stable shellac. A second layer of stable shellac is then added to the layer of pharmaceutical and the process is then repeated to build alternating layers of the pharmaceutical and stable shellac coating. Typically once such a layered capsule is ingested, the outside layer of stable shellac coating will not be dissolved in stomach acid but will be dissolved, over time, in the more alkaline environment of the intestine. Upon dissolution of the outside layer of stable shellac the underlying layer of pharmaceutical composition is absorbed the digestive process begins to dissolve the underlying layer of stable shellac coating. In this step by step digestion portions of the pharmaceutical will be available to the organism over time.

Other substrates are coated with stable shellac using conventional techniques.

What is claimed is:

1. A bleached, stable shellac having a pH of from 5.0 to 6.8;
   and selected from the group consisting of:
   bleached, stable particulate shellac;
   a de-lipidized, bleached, stable shellac solution characterized in that when said solution is heated to 100° F. for 6 weeks, the pH drops less than 15%; and
   a lipidized, bleached stable shellac solution characterized in that when said solution is heated to 100° F. for 6 weeks, the pH drops less than 30%.

2. A bleached, stable shellac of claim 1, wherein the stable shellac is stable particulate shellac.

3. The bleached, stable shellac of claim 2, further characterized in having polymerization time of greater than 1 minute as measured by AUSSIA Polymerization Test.

4. The bleached, stable shellac of claim 3, further characterized in having a Gardner number of less than 18, and an official moisture content of less than 6%.

5. The bleached, stable shellac of claim 4, wherein the polymerization time is greater than 5 minutes as measured by AUSSIA Polymerization Test.

6. The bleached, stable shellac of claim 5, wherein the polymerization time is greater than 10 minutes as measured by AUSSIA Polymerization Test.

7. The bleached stable shellac of claim 5, wherein the acid number is from 65 to 91 and the chloride content is from 1% to 5%.

8. The bleached, stable shellac of claim 1, wherein the stable shellac is the stable particulate shellac, the official moisture content is less than 6%, the polymerization time is greater than 10 minutes as measured by the AUSSIA Polymerization Test, and the Gardner number is less than 9.

9. The bleached, stable shellac of claim 1, wherein the stable shellac is the lipidized stable shellac solution, said solution comprising:
   from 40% to 95% by weight, of a solvent;
   from 5% to 60% by weight, of a stable particulate shellac dissolved in said solvent,
   wherein the bleached stable shellac solution is characterized in that it has a Gardner number of less than 18.

10. The bleached, stable shellac of claim 9, wherein the solvent comprises a volatile organic solvent.

11. The bleached, stable shellac of claim 10, wherein the solvent comprises ethyl alcohol and the Gardner number is less than 9.

12. The bleached, stable shellac of claim 11, wherein bleached stable shellac is free of aminomethylpropanol.

13. The bleached, stable shellac of claim 10, further characterized in that when the bleached stable shellac solution is heated to 100° F. for 6 weeks, the pH drops to not less than 20%.

14. The bleached, stable shellac of claim 1, wherein the stable shellac is the de-lipidized stable shellac solution, said shellac solution comprising:
   from 40% to 95% by weight, of a solvent;
   from 5% to 60% by weight, of a stable particulate shellac dissolved in said solvent,
   wherein the bleached stable shellac solution is characterized in that it has a Gardner number of less than 18.

15. The bleached, stable shellac of claim 14, wherein the solvent comprises a volatile organic solvent.

16. The bleached, stable shellac of claim 15, wherein the solvent comprises ethyl alcohol and the Gardner number is less than 9.

17. The bleached, stable shellac of claim 16, wherein the bleached stable shellac is free of aminomethylpropanol.

18. The bleached, stable shellac of claim 10, further characterized in that when the bleached stable shellac solution is heated to 100° F. for 6 weeks, the pH drops to not less than 13%.

19. A bleached, stable shellac solution, having a pH of from 4.0 up to less than 5.0;
   selected from the group consisting of:
   lipidized, bleached, stable shellac solution, when heated to 40° C. for 30 days, the pH drops and to not less than 3.7;
   and de-lipidized, bleached, stable shellac solution,
   characterized in that said solution when heated to 40° C. for 30 days, the pH drops to not less than 4.2;
   said shellac solution comprising:
   from 40% to 95% by weight, of a solvent; from 5% to 60% by weight, of a stable particulate shellac dissolved in said solvent.

20. The bleached, stable shellac of claim 19, wherein the stable shellac solution is de-lipidized and has a Gardner number of less than 18, the solvent comprises a volatile organic solvent.

21. The bleached, stable shellac of claim 20, wherein the solvent comprises denatured ethyl alcohol, the Gardner number is less than 9, said shellac further characterized in having a drying time of a 35% solution, at 20° C., 50% relative humidity, is less than 35 minutes.

22. The bleached, stable shellac of claim 21, wherein the bleached stable shellac is free of aminomethylpropanol.

23. The bleached, stable shellac of claim 19, wherein the stable shellac solution is de-lipidized and solvent comprises the volatile organic solvent.

24. The bleached, stable shellac of claim 23, wherein the solvent comprises denatured ethyl alcohol, the Gardner number is less than 9, said shellac further characterized in having a drying time of a 35% solution, at 20° C., 50% relative humidity, is less than 35 minutes.

25. The bleached, stable shellac of claim 24, wherein the bleached stable shellac is free of aminomethylpropanol.

26. A method of making stable shellac comprising the following steps:
   providing a liquid pre-shellac; and
   precipitating a stable shellac from the liquid pre-shellac at a pH of from 5.0 to 6.8 to provide a stable particulate shellac.

27. The method of claim 26, wherein the stable shellac is precipitated at a pH from 5.0 to 6.5.

28. The method of claim 27, wherein the stable shellac has a wax content less than 6% of solids weight and a Gardner color of less than 18.

29. The method of claim 26, further comprising the step of:
   solubilizing the stable particulate shellac to form a stable shellac solution.

30. A method of coating a substrate comprising the following steps:
   providing a bleached stable shellac solution selected from the group consisting of:
   a lipidized, bleached stable shellac solution having a pH of from 4 up to less than 5.0 characterized in that when heated to 40° C. for 30 days, the pH drops to not less than 3.7;
   a de-lipidized, bleached stable shellac solution having a pH of from 4 up to less than 5.0 characterized in that when heated to 40° C. for 30 days, the pH drops to not less than 4.2; and
   a lipidized bleached stable shellac solution having a pH of from 5 to 6.8 characterized in that when heated for 6 weeks at 100° F. the pH drops not greater than 30%;
   a de-lipidized bleached stable shellac solution having a pH of from 5 to 6.8 characterized in that when heated for 6 weeks at 100° F. the pH drops not greater than 15%;
   said bleached stable shellac solution comprising:
   from 40% to 95% by weight, of a solvent;
   from 5% to 60% by weight, of a stable particulate shellac dissolved in said solvent,
   applying the stable shellac solution to the substrate;
   evaporating solvent in the stable shellac solution.

31. The method of claim 30, wherein the bleached stable shellac solution is characterized in that it has a Gardner number of less than 18 and the solvent is selected from the group consisting of water, acetone, ethylene glycol butyl ether, methyl propyl carbinol, monohydric alcohols, dihydric alcohols, polyhydric alcohols, propylene glycol, ethylene glycol, diethylene glycol, methanol, ethanol and isopropyl alcohol.

32. The method of claim 31, wherein the solvent comprises ethanol.

33. The method of claim 30, wherein the substrate is selected from the group consisting of: a fruit; a vegetable; a pharmaceutical composition; a confection; and a building material.

34. A coated substrate comprising:
   a substrate;
   a bleached stable shellac coating disposed on the substrate wherein the coating has a hardness of from 100 to 200 Konig units, a pH of greater than 4, and a Gardner color of less than 18.

35. The substrate of claim 34, wherein the substrate is selected from the group consisting of: a fruit, a vegetable; a pharmaceutical composition; confection; and a building material.

36. A substrate coated with shellac of claim 1.

37. A substrate coated with shellac of claim 19.

* * * * *